(12) United States Patent
Bausmith, III (10) Patent No.: US 7,581,559 B2
(45) Date of Patent: Sep. 1, 2009

(54) CHECK VALVE FOR A FLUID ADMINISTRATION SYSTEM

(75) Inventor: William E. Bausmith, III, Batavia, OH (US)

(73) Assignee: Mallinckrodt Inc., St. Louis, MO (US)

( * ) Notice: Subject to any disclaimer, the term of this patent is extended or adjusted under 35 U.S.C. 154(b) by 272 days.

(21) Appl. No.: 10/794,358

(22) Filed: Mar. 5, 2004

(65) Prior Publication Data

US 2005/0194047 A1    Sep. 8, 2005

(51) Int. Cl.
F16K 15/14    (2006.01)

(52) U.S. Cl. .................. 137/512; 137/515; 137/843; 137/852; 604/236; 604/247

(58) Field of Classification Search ............. 137/515, 137/515.5, 515.7, 843, 852, 112, 896, 861, 137/872, 863, 512; 604/30, 236, 247, 533, 604/537, 258; 251/142
See application file for complete search history.

(56) References Cited

U.S. PATENT DOCUMENTS

| | | | | |
|---|---|---|---|---|
| 3,196,890 | A | * | 7/1965 | Brandenberg .............. 137/102 |
| 3,572,375 | A | | 3/1971 | Rosenberg |
| 3,633,605 | A | * | 1/1972 | Smith ........................ 137/113 |
| 4,252,116 | A | * | 2/1981 | Genese et al. ................. 604/81 |
| 4,904,245 | A | | 2/1990 | Chen et al. |
| 4,946,448 | A | * | 8/1990 | Richmond .................. 604/247 |
| 5,176,658 | A | * | 1/1993 | Ranford ...................... 604/247 |
| 5,267,964 | A | * | 12/1993 | Karg ........................... 604/141 |
| 5,665,074 | A | | 9/1997 | Kelly |
| 5,697,904 | A | * | 12/1997 | Raines et al. ................ 604/247 |
| 5,743,872 | A | | 4/1998 | Kelly |
| 6,290,682 | B1 | * | 9/2001 | Myers ......................... 604/247 |
| 6,896,002 | B2 | * | 5/2005 | Hart et al. .................. 137/625.5 |
| 2003/0122095 | A1 | * | 7/2003 | Wilson et al. .................. 251/12 |

FOREIGN PATENT DOCUMENTS

| | | |
|---|---|---|
| DE | 19816398 | 10/1999 |
| EP | 1091164 | 4/2001 |
| WO | 8401805 | 5/1984 |

OTHER PUBLICATIONS

International Search Report.

* cited by examiner

*Primary Examiner*—Kevin L Lee
(74) *Attorney, Agent, or Firm*—Wood, Herron & Evans, LLP (57) ABSTRACT

A check valve for a fluid administration system. A connector includes a housing, and first and second conduits defined by the housing, wherein the first conduit is in fluid communication with the second conduit. A check valve is disposed within the housing and includes a first body portion defining a first passageway for fluid flow, and a second body portion defining a second passageway for fluid flow. The first and second passageways are in fluid communication with one another and the second body portion is movable relative to the first body portion between first and a second positions. When the second body portion is in the first position, fluid flow may occur in a first direction, but not in a second direction substantially opposite to the first direction. When the second body portion is in the second position, fluid flow may occur in the second direction.

46 Claims, 6 Drawing Sheets

CHECK VALVE FOR A FLUID ADMINISTRATION SYSTEM

FIELD OF THE INVENTION

The present invention relates generally to check valves, and more particularly, to fluid administration systems which include check valves.

BACKGROUND OF THE INVENTION

Maintaining and controlling fluid flow is important in many apparatus and procedures, including medical procedures, in order to ensure that a fluid medication is delivered to a particular location, such as from a fluid source into a subject patient. In delivering a fluid to a patient through a fluid administration system, it is often important to ensure that the fluid moves in one direction, generally from the fluid source to the patient, due to myriad problems that can arise should fluid flow be reversed during an injection procedure. In order to prevent the reversal of fluid flow, many fluid administration systems include check valves. A check valve may be disposed within a fluid flow passageway and include structure that may only allow fluid flow in a first direction, while preventing any fluid flow in an opposite, second direction. Certain conventional check valves may include a mechanism to allow fluid flow in the reverse direction. However, for safety purposes, the check valves that are included in medical apparatus generally allow fluid flow only in a first direction, from fluid source to patient.

A common problem of conventional check valves is that upon reversal of liquid flow through tubing in a direction from a patient to a fluid source, the check valves fail to respond as quickly as desired to move into a closed position. Further, many conventional check valves require some positive action by an operator to open a check valve, and another positive action by an operator to close the check valve. In a procedure, such as a medical injection procedure, this increases the risk that a check valve may inadvertently be left in an open position. That is, should such conventional check valves be used, there is always the risk of backflow from the output to the input of the fluid administration system, which in many instances is very undesirable, and in some cases, may even be fatal.

Thus, it can be seen that preventing fluid flow from the output to the input of a fluid administration system can be very important. As a result, valves in medical injection systems may be made to be normally closed, whereby the valve, in order to remain open, must be subject to a high flow pressure. When fluid flows from the fluid source to the patient in the forward direction, the flow pressure moves the valve to an open position to allow such flow. When the flow pressure is decreased, the valve will quickly close. However, as will be explained in greater detail below, there are many instances in which an operator may wish to open a check valve in order to reverse fluid flow from the output to the input. The normally closed types of fluid check valves used in medical procedures do not allow for the valve to be opened in these instances.

As mentioned briefly above, during an injection, fluid flow is required to be directed into a patient. The procedure generally involves directing fluid flow from a fluid input device, such as a syringe, through a delivery tube, then into and through a fluid output device, such as a catheter, to deliver a particular fluid into a subject patient. During the setup of the injection system, a medical technician will need to confirm that a catheter which is inserted into a patient is in the correct position. The technique used to determine correct catheter placement is for the syringe plunger to be momentarily retracted until blood is detected in the tube, thereby confirming correct catheter placement in a blood vessel. With the standard normally closed check valves in place in current fluid administration systems, backing up the syringe plunger and thus drawing a fluid, such as blood, through the catheter and into the delivery tube is impossible.

Another problem with the use of normally closed check valves in a fluid administration system is that some syringes require returning the plunger to the starting position of an injector following injection in order for the syringe to be removed from the injector. As described above, the standard normally closed check valves prevent retraction of the syringe plunger. Thus, in current injection systems, the delivery tube including the check valve requires disconnection from the syringe in order to retract the plunger up to its starting point for removal of the syringe. The removal of the delivery tube has the potential to expose the medical technician to biohazards, such as blood or other bodily fluids.

An example of check valves as used in medical fluid administration systems is disclosed in U.S. Pat. Nos. 5,743, 872 and 5,665,074 by Larry Kelly and assigned to Liebel-Flarsheim Company of Cincinnati, Ohio. The '872 and '074 patents disclose a limited backflow reflux valve for connection between a syringe, catheter, and bulk container of injection fluid. This reflux valve permits injection of fluid from the syringe through the catheter into the patient, and also permits refilling of the syringe from the bulk container without disconnection of any tubing. Although the reflux valve also permits limited volume of fluid to backflow from the catheter into the syringe, so that the catheter may be checked for patency, it prevents any further backflow along this path after a limited volume has been allowed. Thus, such a limited backflow reflux valve, as in the '872 and '074 patents, would not allow the reversal of fluid flow such as would be required to allow a syringe plunger to be completely backed up within the fluid administration system, such as for subsequent disconnection from an injection system. Nor does the limited backflow reflux valve of the '872 and '074 patents allow a fluid to flow in a reverse direction through or past the valve.

Other injection procedures may require the use of multiple syringes. Additional problems are raised by these injection procedures. The use of multiple syringes not only increases the possibility of backflow from the output to the input due to the increased number of delivery tubes and syringes, but also includes the additional drawback that a first fluid from a first syringe or first delivery tube may undesirably mix with a second fluid from a second syringe or second delivery tube (or alternatively, that air in a first delivery tube may be introduced into fluid in a second delivery tube, and from there into a patient, with possibly drastic consequences). An example of such first and second fluids may be a saline solution and contrast media, which are used during imaging procedures. Saline is normally used during a body pre-scan prior to the injection of contrast media. The pre-scan is used for digital subtraction or superposition of images. This process results in enhancing the final image of a scan. In order to prevent the degradation of the final image, the introduction of contrast media into the saline during the pre-scan procedure should be prevented. However, in fluid administration systems including conduits for both saline and contrast media, the likelihood of mixture of the two fluids is somewhat high due to the configuration of the fluid administration system, as will now be generally described.

In order to include multiple syringes, each having a delivery tube, in a fluid administration system, connectors are often used to direct fluid flow from the multiple input delivery tubes into a single output delivery tube which carries fluid into a patient. Such connectors are widely employed in industrial and medical applications to releasably and lockably interconnect fluid delivery tubes. For example, a first delivery tube for a first fluid like saline and a second delivery tube for a second fluid like contrast media may be placed in fluid communication with one another through the use of a connector. Connectors are often used due to their reliability, their low cost, their ease of assembly, and high pullout forces which resist separation. In particular, the Y-connector is the commonly used shape for introducing fluids in a medical injection system due to the reduction of flow turbulence under high flow rate conditions. Flow turbulence will reduce system performance.

In current injection systems, such as those described above, check valves are disposed within the system to aid in preventing mixing of fluids such as saline and contrast media. The position of the check valve in the injection system determines if any contrast media will be exposed to the saline and delivered during a pre-scan. Normally, the exit side of a check valve will have an area where either air or contrast media can collect. This area may be referred to as a "dead zone." Since the injection of air is extremely problematic from a patient safety perspective, contrast media is used to remove the air on the exit side of the check valve by flooding the delivery tubes in proximity to the check valve with contrast media. This procedure places contrast media on the exit side of the check valve, which creates the potential for introduction of contrast media into the saline stream, and thus into a subject patient before it is required. Introduction of this contrast media during a pre-scan may alter the final composite image due to false highlighting. In order to prevent degrading the composition image, exposure of the contrast media to saline during the pre-scan phase of an injection procedure should be prevented. However, as described above, with the presence of contrast media on the exit side of the check valve, to prevent air from being injected into a patient, the contrast media mixes with the saline solution during a pre-scan procedure.

This problem of image degradation is further compounded by the fact that there are relatively large dead zones in medical injection systems including connectors. This is because present connectors do not include check valves disposed within the body of the connector. Rather, check valves in present medical injection systems are located in the delivery tubing on the input side of the connector. As a result, a dead zone is present from the exit side of the check valve through any remainder of the input delivery tubing, and through the fluid conduit present in the connector to which the input delivery tubing is connected. As described above, this entire area may be filled with contrast media in order to prevent the introduction of air during an injection. As a result, this relatively large amount of contrast media may be introduced to saline during a pre-scan, thereby degrading the final image.

Thus, it would be desirable to provide a check valve which is normally closed but which may be opened to allow reverse fluid flow to back up a syringe plunger so that catheter placement may be confirmed, and in order to reduce the risk of biohazard resulting from removal of an extension tube to back up the syringe plunger following an injection. It would be further desirable to provide a connector system which prevents air from being injected into a patient and also prevents the mixture of contrast media with saline during a pre-scan procedure.

SUMMARY OF THE INVENTION

The present invention eliminates the problems and drawbacks with fluid administration systems as described above in the Background of the Invention.

In a first aspect, the present invention provides a check valve for a fluid administration system which may be selectively adaptable to allow or not allow fluid flow from a fluid output to a fluid input through the check valve. In one embodiment, the check valve may be opened to permit fluid flow from an output to an input. Thus, during a medical injection procedure the check valve may be opened to allow fluid to flow from the exit point proximal the patient, through the check valve, and to the syringe input, in order to check for correct catheter placement, for example.

The check valve of the present invention includes a first body portion that defines a first passageway for fluid flow. The check valve further includes a second body portion defining a second passageway for fluid flow. This second body portion is disposed in cooperative relationship with the first body portion such that the first passageway and second passageway are in fluid communication with one another. The first and second body portions may also be movable relative to one another. A diaphragm may be disposed within the path of fluid flow and may be movable between a closed position and an open position. When the second body portion is in a first position relative to the first body portion, the check valve is closed. However, when the second body portion is moved to a second position relative to the first body portion, the check valve is open. When the check valve is in the closed position, fluid flows through the check valve in a first direction. When the check valve is in the open position, fluid flow may be reversed in a second direction. Such reversal of fluid flow allows for backing up a syringe plunger to confirm catheter placement or to remove a syringe from an injection system.

The second body portion is adapted to be manually moved toward the first body portion in order to open the check valve. This may be accomplished by grasping the second body portion and pushing it toward the first body portion The second body portion may be adapted to return to the first position upon its release. This prevents the check valve form being inadvertently left in the open position.

Further, the check valve may include a sleeve including an orifice adapted to receive at least a portion of the second body portion. The sleeve may be movable relative to the first and/or second body portions. In one embodiment, the sleeve may further include a cam surface, which may be positionable in an engaged position or a disengaged position. When the sleeve is placed in the disengaged position, the diaphragm of the check valve of the present invention is in a closed position, and when the sleeve is placed in the engaged position, the second body portion may be cooperatively moved to place the diaphragm in an open position. In particular, the cam surface of the sleeve may engage or disengage the second body portion to move the second body portion relative to the first body portion. This sleeve may be operated manually. Thus, through actuation of the sleeve, the check valve may be manually controlled to open in order to allow reverse fluid flow. Thus, the sleeve may be used as an alternative method of opening the check valve.

In a second aspect, the present invention may include a connector including a check valve disposed within the connector. By placing a check valve within the connector, dead zone may be reduced and eliminated. More specifically, the connector includes a housing which defines first, second, and third fluid conduits. The first fluid conduit may interact with and may be in fluid communication with the second fluid conduit. Either or both of the first and second fluid conduits may be in fluid communication with the third conduit. The check valve is disposed within the housing. The check valve may be positioned within the fluid flow of the first fluid conduit. The exit side of the check valve may be positioned immediately adjacent to the second fluid conduit. In particular, a diaphragm of the check valve may be positioned at the intersection of the first and second fluid conduits. The check valve may be movable between a closed and an open position. Since the diaphragm is positioned at the intersection point of the first and second fluid conduits of the connector, the introduction of a first fluid, such as contrast media, may occur directly into the second fluid conduit. As a result, there is no dead zone area on the exit side of the check valve. Thus, air can be removed from the system while not exposing contrast to the saline. In particular, air can be removed by saline flow itself, leaving no space for air to collect, and eliminating the need to introduce contrast media during the pre-scan procedure.

In one particular embodiment of this aspect of the present invention, the diaphragm may be of an elliptical shape. This elliptical shape allows the overall size of the connector to be reduced. The smaller size of the connector provides many benefits, such as better appearance, less material to produce, and less cost to produce.

In another embodiment of this aspect of the present invention, the connector may include a plurality of check valves disposed within the housing. The connector of this embodiment present invention includes a housing and first, second, and third fluid conduits defined by the housing. The first fluid conduit is disposed such that it interacts with and is in fluid communication with the third fluid conduit. The second fluid conduit is disposed such that it also interacts with and is in fluid communication with the third fluid conduit. A first check valve may be positioned within the fluid flow of the first fluid conduit, and a second check valve may be positioned within the fluid flow of the second fluid conduit. The exit end of the first check valve may be positioned immediately adjacent to the third fluid conduit. The exit end of the second check valve may also be positioned immediately adjacent to the third fluid conduit. In particular, a first diaphragm of the first check valve may be positioned at the intersection of the first and third fluid conduits and a second diaphragm of the second check valve may be positioned at the intersection of the second and third fluid conduits. Each of the first and second check valves may be movable between a closed and an open position. In addition to the benefits of a connector including a check valve described above, the use of first and second check valves also allows for the use of fluid administration systems having multiple syringes having differing pressure ratings, attached to the first and second fluid conduits. The check valves prevent the pressure of a first syringe from affecting a second syringe or fluid conduit.

In another aspect, the present invention provides a fluid administration system including a fluid input device (such as a syringe), a fluid output device (such as a catheter), a delivery tube, and a check valve operatively connected to the delivery tube. The delivery tube includes first and second ends with the first end being connected to the fluid input device. The second end of the delivery tube may be connected to the fluid output device. The check valve may be adapted to be opened and closed manually. Additionally, the fluid administration system may include a connector and second and third delivery tubes. Each of the second and third delivery tubes each also have a first end and a second end. The fluid administration system may be configured such that a first fluid input device is operatively connected to the first end of the first delivery tube, and a second fluid input device is operatively connected to the first end of the second delivery tube. The second ends of the first and second delivery tubes are operatively connected to the connector. The first end of the third delivery tube is operatively connected to the connector, and the second end of the third delivery tube is operatively connected to the fluid output device.

These and other advantages of the application will be apparent to those of skill in the art with reference to the drawings and the detailed description below.

DETAILED DESCRIPTION OF THE INVENTION

Referring now to the Figures, the present invention overcomes the drawbacks with current fluid administration systems, as described above in a first aspect, by providing a check valve 10 which may be activated to allow for reversal of fluid flow in order to enhance the operation of a fluid administration system. In particular, the check valve 10 may be selectively adaptable to either allow or not allow fluid flow from a fluid output, to a fluid input, through or past the check valve 10. The present invention, in a second aspect, provides a connector 12 that may be used in a fluid administration system. The connector 12 includes a check valve 10 to reduce and eliminate dead zones which exist in prior art connectors of fluid administration systems.

Figure 1:
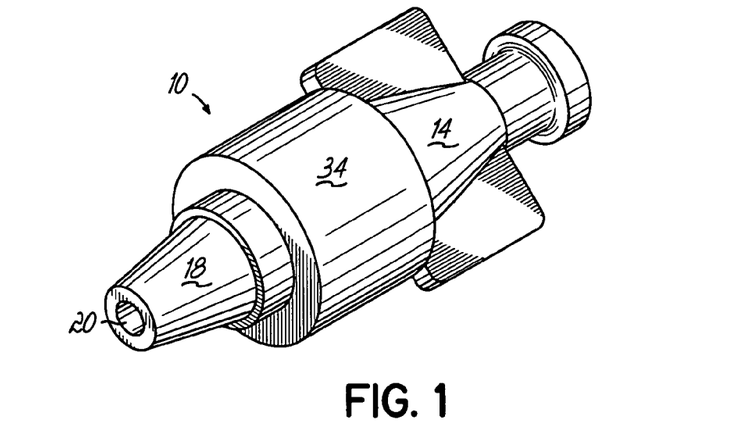
FIG. 1 is a perspective view of a check valve having manual activation in accordance with the principles of the present invention.
Figure 2:
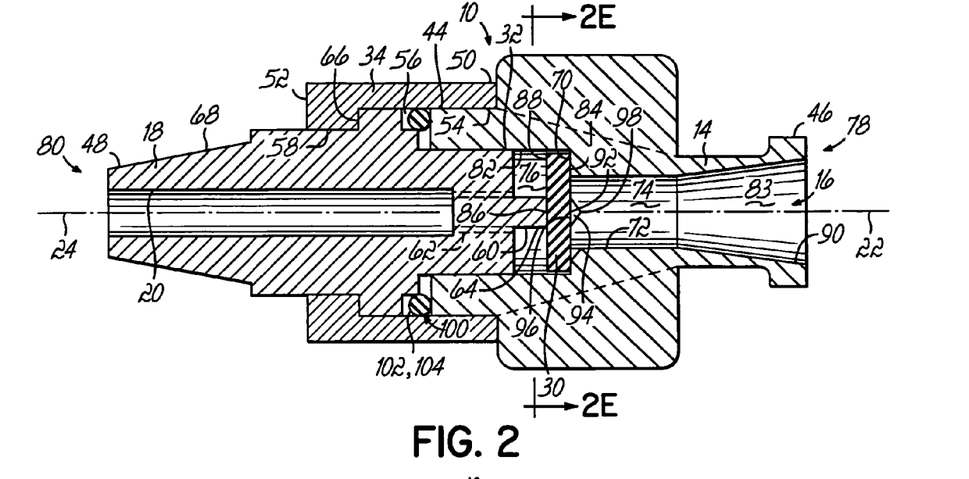
FIG. 2 is a side cross-sectional view of the check valve of FIG. 1, showing the check valve in the closed position, in accordance with the principles of the present invention.
Figure 3:
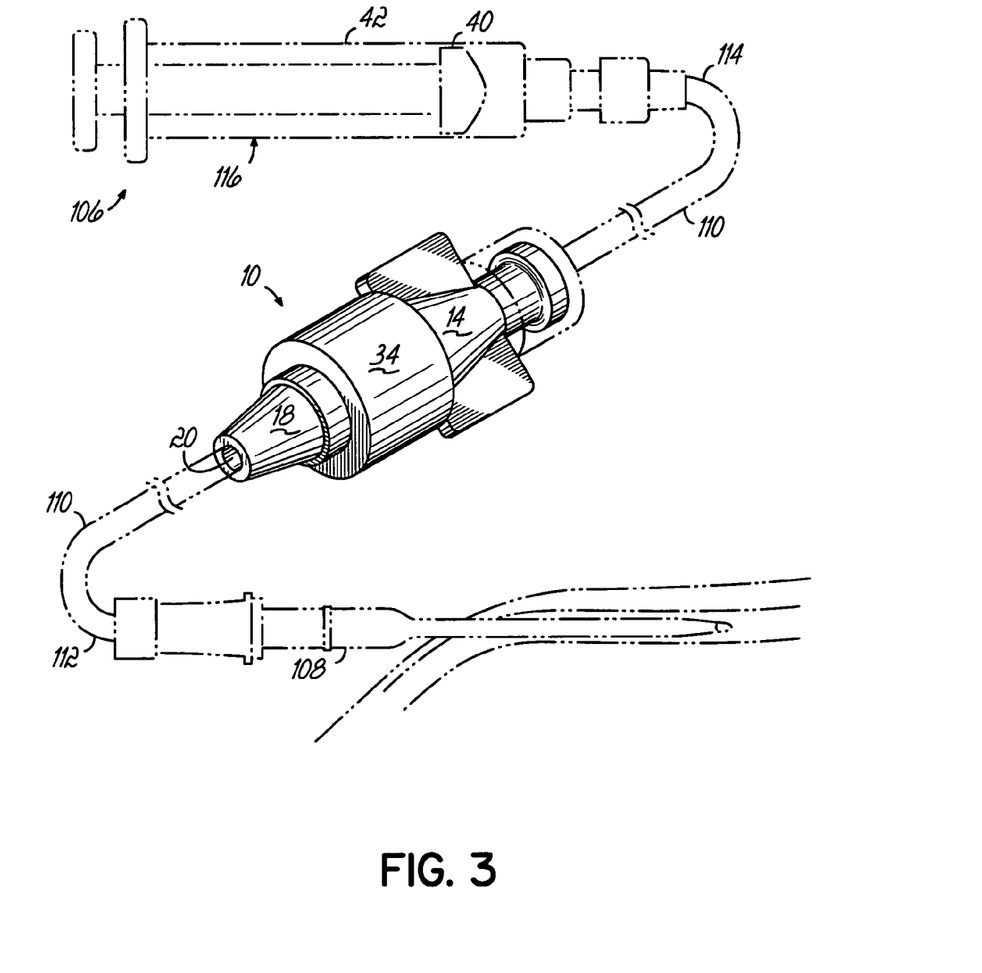
FIG. 3 is a schematic showing an injection system, in accordance with the principles of the present invention.
Figure 4:
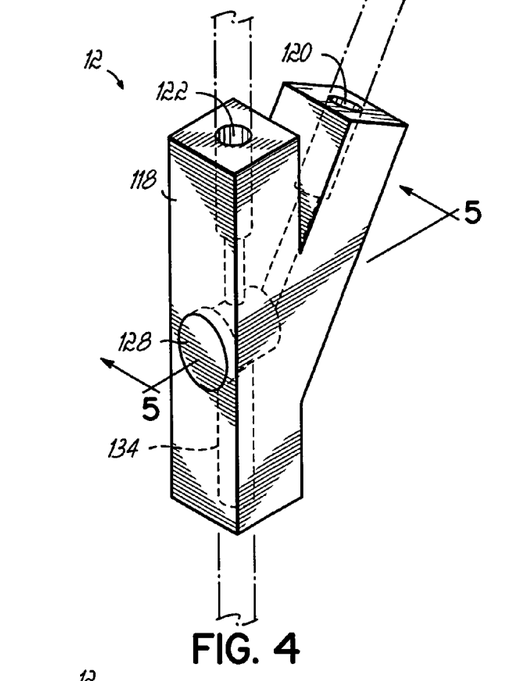
FIG. 4 is a perspective view of a connector having an integral check valve in accordance with the principles of the present invention.

Referring to FIGS. 1-3, in one aspect, the present invention provides a check valve 10 in a fluid administration system which is normally closed to allow fluid flow in a single direction, but which may be selectively opened in order to allow for reversal of fluid flow. The check valve 10 may be configured to automatically return to a closed position once reverse fluid flow is complete. The check valve 10 of the illustrated embodiment includes a first body portion 14 that defines a first passageway 16 for fluid flow. The check valve 10 further includes a second body portion 18 that defines a second passageway 20 for fluid flow. The second body portion 18 is disposed in cooperative relationship to the first body portion 14, such that the first passageway 16 and the second passageway 20 are adapted to be in fluid communication with one another. In the illustrated embodiment, the first and second passageways 16, 20 are substantially coaxial relative to one another along their longitudinal axes 22, 24. However, it will be recognized that such a coaxial relationship is not necessary, as long as the first and second passageways 16, 20 are adapted to be in fluid communication with one another. The first and second body portions 14, 18 may be movable relative to one another. In particular, in the illustrated embodiment, the second body portion 18 is movable relative to the first body portion 14 between a first position and a second position. When the second body portion 18 is in the first position, fluid flow may occur in a first direction 26, but not in a second direction 28. The first direction 26 is generally from an input, such as a fluid source within a fluid input device, to an output, such as a fluid output device, for example, a catheter. The second direction 28 is substantially opposite to the first direction 26. When the second body portion 18 is in the second position, fluid flow may occur in the second direction 28. Second directional fluid flow may occur from an output device, through or past the check valve 10, and to a fluid input device.

A diaphragm 30 may be disposed in the check valve 10 in order to allow or prevent the flow of fluid in a particular direction. In the illustrated embodiment, the diaphragm 30 is a disc diaphragm positioned at a proximal end 32 of the second body portion 18 and within the first passageway 16 of the first body portion 14 in the path of fluid flow. While the diaphragm 30 of the illustrated embodiment is disposed within the first body portion 14, it will be recognized that such positioning is not necessary, and that the diaphragm 30 may alternatively be placed within the second body portion 18, or between the first and second body portions 14, 18, or with at least a portion disposed within both the first and second body portions, 14, 18, for example. It will be recognized that any configuration of the check valve 10 wherein the diaphragm 30 is positioned such that it blocks fluid flow in a second direction 28 when in a first position, and allows fluid flow in a second direction 28 when in a second position, is suitable for the present invention. Further, the illustrated diaphragm 30 is a disc diaphragm. However, it will be recognized by those of skill in the art that other diaphragms such as umbrella diaphragms, may be used. The diaphragm 30 may be movable between an open position and a closed position.

A sleeve 34 may be operatively connected to the first and/or second body portions 14, 18. In the illustrated embodiment, the sleeve 34 substantially surrounds at least a portion of both the first body portion 14 and the second body portion 18. In one embodiment, the sleeve 34 may include a cam surface 36. The sleeve 34 may be positionable relative to the second body portion 18 in either an engaged position, wherein the cam surface 36 contacts the second body portion 18, or a disengaged position, wherein the cam surface 36 does not contact the second body portion 18. Further, when the sleeve 34 is in the disengaged position, the second body portion 18 is in the first position. When the sleeve 34 is in the engaged position, the second body portion 18 is in the second position.

The sleeve 34 may be rotatable relative to the remainder of the check valve 10. Rotation of the sleeve 34 may vary the interaction of the cam surface 36 with the second body portion 18 in order to allow for fluid flow in the first or second direction 26, 28, as will be described in greater detail below. In an alternate embodiment, the second body portion 18 may be manually moved toward the first body portion 14, to allow fluid flow in the second direction 28, without the use of a cam surface 36 and without the use of the sleeve 34. In yet another alternative embodiment, the sleeve 34 may be used to move the second body portion 18 from the first position to the second position without the use of a cam surface 36.

The diaphragm 30 may selectively block fluid flow in a particular direction or allow fluid flow in a particular direction. The diaphragm 30 may be positioned within the check valve 10 in a closed position or an open position. When the diaphragm 30 is in the closed position, fluid flow may only proceed in the first direction 26. The force of fluid flow in the first direction 26 moves or alters the diaphragm 30 in order to flow past the diaphragm 30. However, any attempted fluid flow in the second direction 28 will be blocked by the diaphragm 30, when the diaphragm 30 is in the closed position.

When the diaphragm 30 is in the open position, fluid flow may proceed in the second direction 28. When in the open position, the diaphragm 30 is moved or altered in order to allow fluid to flow past the diaphragm 30 in the second direction 28. When the diaphragm 30 is in the open position, fluid flow may also occur in the first direction 26.

In one embodiment of the present invention, the check valve 10 can be manually opened or closed by moving the diaphragm 30 cooperatively with movement of the second body portion 18. In the illustrated embodiment, movement of the second body portion 18 may be caused by movement of the sleeve 34. In particular, in the illustrated embodiment, the sleeve 34 may be freely rotatable about its axis of symmetry 38. The diaphragm 30 of the check valve 10 of the present invention may be normally closed. This allows for fluid flow only in a first direction 26 from a fluid source and into a patient. In the illustrated embodiment, this first direction 26 proceeds from the first body portion 14 to the second body portion 18. As described above, the diaphragm 30 may prevent fluid from flowing in a second direction 28 away from a patient, such as would be caused by retracting a plunger 42 of a syringe 40 connected to a fluid flow or injection apparatus, for example. However, by rotating the sleeve 34 into the engaged position, the cam surface 36 of the cam may cause the second body portion 18 to move longitudinally with respect to the first body portion 14 of the check valve 10. Since the second body portion 18 is operatively connected to the diaphragm 30, the diaphragm 30 moves cooperatively with the second body portion 18. In the illustrated embodiment, the diaphragm 30 is moved toward the first body portion 14 to an open position, as will be described in greater detail below. This allows fluid flow from the second body portion 18 to the first body portion 14 in the second direction 28.

Figure 2A:
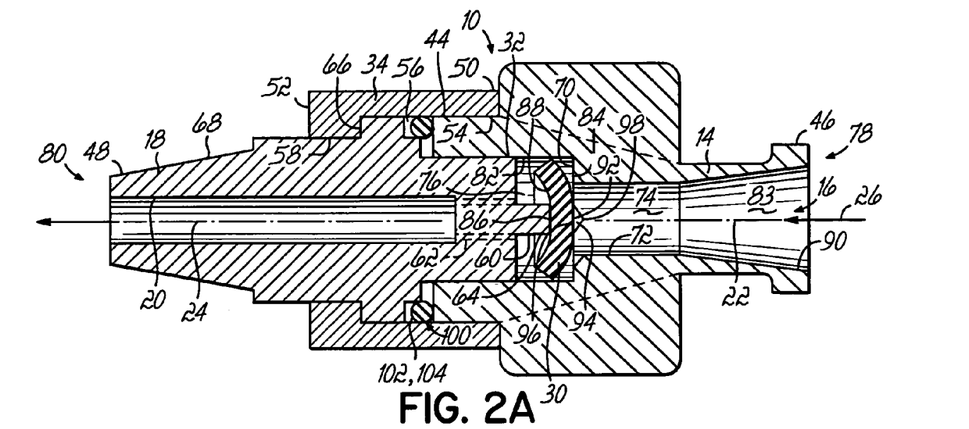
FIG. 2A is a side cross-section view of the check valve of FIG. 1, showing the check valve in the closed position with fluid flow occurring in a first direction, in accordance with the principles of the present invention.
Figure 2B:
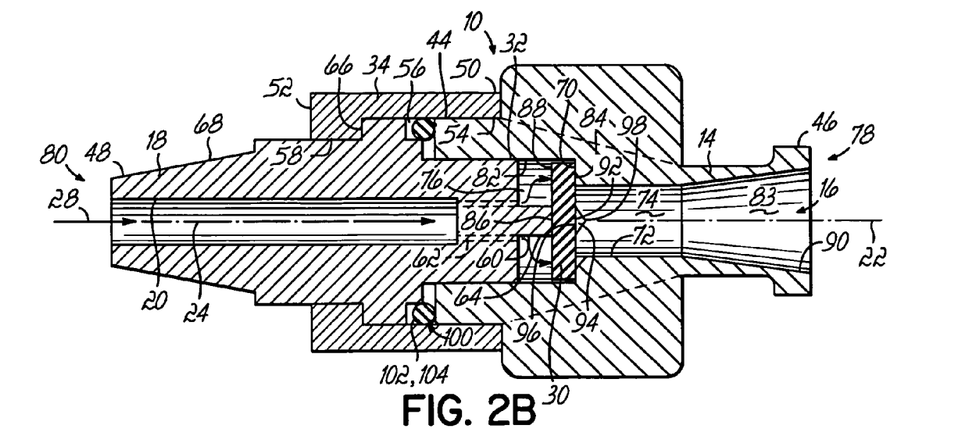
FIG. 2B is a side cross-section view of the check valve of FIG. 1, showing the check valve in the closed position with attempted fluid flow in a second direction, in accordance with the principles of the present invention.
Figure 2C:
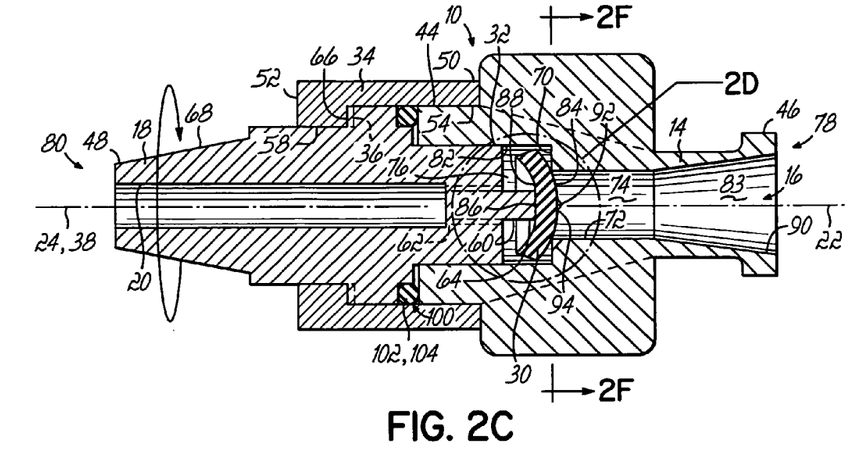
FIG. 2C is a side cross-sectional view of the check valve of FIG. 1 in the open position, to allow fluid flow to occur in a second direction, in accordance with the principles of the present invention.
Figure 2D:
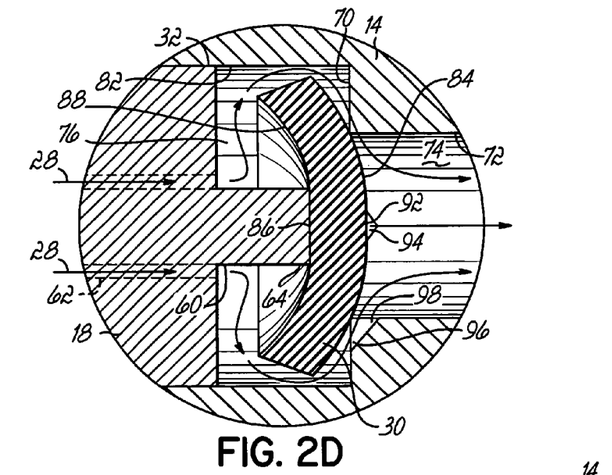
FIG. 2D is an enlarged side cross-sectional view of a portion of FIG. 2C, showing the check valve in the open position with fluid flow occurring in a second direction, in accordance with the principles of the present invention.
Figure 2E:
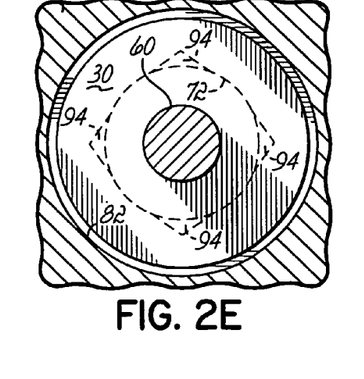
FIG. 2E is a cross-section taken along lines 2E-2E of FIG. 2 with the check valve in the closed position, in accordance with the principles of the present invention.
Figure 2F:
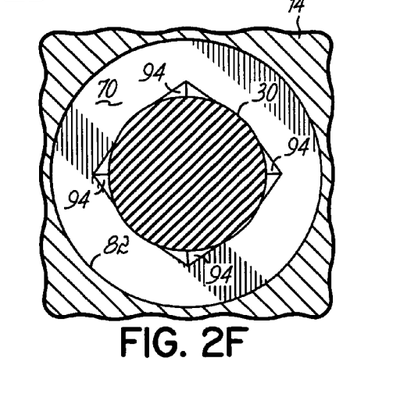
FIG. 2F is a section-section taken along lines 2F-2F of FIG. 2C with the check valve in the open position, in accordance with the principles of the present invention.

Referring in particular to FIGS. 2-2F, the operation of the check valve 10 of the illustrated embodiment to allow fluid flow in the second direction 28 will now be described in greater detail. The first body portion 14 includes a distal end 44 and a proximal end 46. The first passageway 16 extends throughout the first body portion 14. The second body portion 18 has a proximal end 32 and a distal end 48. The proximal end 32 of the second body portion 18 may be received by the first passageway 16 at the distal end 44 of the first body portion 14. The second passageway 20 extends through the second body portion 18. The sleeve 34 includes a proximal end 50 and a distal end 52, with a first opening 54 formed in the proximal end 50, and a sleeve passageway 56 extending throughout and terminating at a second opening 58 at the distal end 52 of the sleeve 34. The second body portion 18 is received within the second opening and protrudes distally therefrom. The distal end 44 of the first body portion 14 is received by the second opening 58 at the proximal end 50 of the sleeve 34.

In the illustrated embodiment, the proximal end 32 of the second body portion 18 includes a post 60 that extends in a proximal direction toward the first body portion 14, when the first and second body portions 14, 18 are in receiving relationship. The second body portion 18 includes at least one minor fluid conduit 62 near the post 60 which may allow for continuous fluid flow in the first direction 26 from the first passageway 16 to the second passageway 20. The diaphragm 30 of the check valve 10 is disposed adjacent to the proximal end 64 of the post 60 and within the first passageway 16. Alternatively, the diaphragm 30 may be operatively connected to the post 60. As described above, the second body portion 18 may be movable from a first position to a second position. As this occurs, the diaphragm 30 may move cooperatively therewith. Movement of the diaphragm 30 in response to fluid flow can operate to allow fluid flow in a first direction 26, but prevent fluid flow in a second direction 28, when the sleeve 34 is in the first position. However, when the sleeve 34 is in the second position, the placement of the diaphragm 30 within the check valve 10 is altered such that fluid flow may occur in the second direction 28.

In the illustrated embodiment, the sleeve 34 may be used to move the second body portion 18 from the first position to the second position. As can be seen from the figures, and particularly with reference to FIG. 2C, the sleeve 34 may include a cam surface 36 which is adapted to contact and confront a first shoulder 66 formed on an exterior surface 68 of the second body portion 18. When the sleeve 34 is in the first position such that the cam surface 36 does not confront the first shoulder 66 of the second body portion 18 (as depicted in FIG. 2), the diaphragm 30 is positioned such that it may seat against a second shoulder 70 formed on an interior surface 72 of the first passageway 16 of the first body portion 14. In the illustrated embodiment, this second shoulder 70 is formed between a first segment 74 and a second enlarged segment 76 of the first passageway 16. It further can be seen that in the illustrated embodiment, the diaphragm 30 is disposed such that it is substantially perpendicular to the longitudinal axis 22 of the first passageway 16. However, it is not necessary that the diaphragm 30 be substantially perpendicular, but merely that it be positioned to prevent fluid flow in the second direction 28 when the second body portion 18 is in the first position. When the sleeve 34 is in this first position, the check valve 10 is closed, such that fluid flow in a first direction 26 may occur, but fluid flow in a second direction 28 does not occur.

Referring now to FIG. 2A, the check valve 10 with the second body portion 18 in the first position is depicted when subjected to fluid flow in a first direction 26 (such as from a fluid source to a patient). Fluid flow in the first direction 26 occurs from the proximal end 78 to the distal end 80 of the check valve 10 as shown in the figures. Thus, fluid initially enters the first passageway 16 within the first body portion 14. The fluid then flows from the first passageway 16 of the first body portion 14 into the second passageway 20 of the second body portion 18. As can be seen from the figures, and as described above, the diaphragm 30 is disposed in the check valve 10 within the path of fluid flow. In particular, in the illustrated embodiment, the diaphragm 30 is positioned adjacent the post 60 of the second body portion 18 and within the second enlarged segment 76 of the first passageway 16. In the illustrated embodiment, the diaphragm 30 is flexible. As fluid flows through the check valve 10 in the first direction 26, the pressure of the fluid causes the diaphragm 30 to deform in a distal direction, as seen in FIG. 2A. As this occurs, fluid may flow around the now-deformed diaphragm 30 and thereafter into the second passageway 20 within the second body portion 18. In particular, in the illustrated embodiment, fluid flows past the diaphragm 30 and into the most distal portion 82 of the first passageway 16. Fluid flows then through the minor fluid conduit 62 adjacent to the post 60, and from there to the second passageway 20. Thus, fluid may flow unimpeded in the first direction 26 from the proximal end 78 of the check valve 10 to the distal end 80 of the check valve 10.

Referring now to FIG. 2B, the check valve 10, with the second body portion 18 in the first position, is shown with fluid flow in a second direction 28 being attempted. Any such attempted fluid flow in a second direction 28 occurs from the distal end 80 of the check valve 10 to the proximal end 78 of the check valve 10. As fluid enters from the distal end of the second fluid flow passageway, it moves then through the minor fluid conduit 62 adjacent the post 60, and into the distal portion 82 of the first passageway 16. Once the fluid has entered the distal portion 82 of the first passageway 16, it will then confront the diaphragm 30. As described above, the diaphragm 30 is flexible. If deformation of the diaphragm 30 occurs, fluid flow would cause the diaphragm 30 to deform in the proximal direction, allowing fluid to pass into the proximal end of the first fluid passageway 16. However, when the second body portion 18 is disposed in the check valve 10 in the first position, at least a portion of a proximal surface 84 of the diaphragm 30 contacts and confronts the second shoulder 70 formed between the first segment 74 and the second enlarged segment 76 within the first passageway 16. As a result, the diaphragm 30 cannot deform in the proximal direction. In the absence of any deformation, the diaphragm 30 completely blocks the fluid from entering the proximal portion 83 of the first passageway 16, thereby preventing fluid flow in the second direction 28.

Referring now to FIG. 2C, the check valve 10 is shown with the second body portion 18 disposed in a second position, to allow for fluid flow in the second direction 28. As can be seen from FIG. 2C, when the second body portion 18 is moved from the first to the second position, it is moved in a direction toward the proximal end 78 of the check valve 10. The post 60 of the second body portion 18 confronts and contacts a central portion 86 of the distal surface 88 of the diaphragm 30. Movement of the second body portion 18, and thus the post 60 toward the proximal end 78 of the check valve 10, forces the diaphragm 30 to move toward the proximal end 78 of the check valve 10. In particular, the diaphragm 30 will attempt to be moved from the second enlarged segment 76 of the first passageway 16 into the first segment 74 of the first fluid passageway 16. However, as can be seen from the figures, the diaphragm 30 is greater in size than the area of the first segment 74 of the first passageway 16. This causes the diaphragm 30 to deform in the distal direction. As will be explained in greater detail below this allows fluid to flow in the second direction 28.

Movement of the second body portion 18 from the first position to the second position can be achieved manually by directly grasping an exposed area of the second body portion 18 and pushing it toward the proximal end 78 of the check valve 10. Alternatively, and as can be seen in the illustrated embodiment, the cam surface 36 may be used to move the second body portion 18 from the first position to the second position. As can be seen in FIG. 2C, the sleeve 34 has been rotated such that the cam surface 36 contacts and confronts the first shoulder 66 of the second body portion 18. The second body portion 18 thus moves due to the influence of the cam surface 36 toward the proximal end 78 of the check valve 10. When the check valve 10 is in this second position, fluid flow in a second direction 28 from the distal end 80 of the check valve 10 to the proximal end 78 of the check valve 10 may occur. It will be recognized that in an alternate embodiment, the cam surface 36 may be disposed on the second body portion 18, as opposed to on the sleeve 34.

Referring to FIGS. 2C, 2D, and 2F, the second body portion 18 in the second position and fluid flow in the second direction 28 is shown. The second body portion 18 has been moved, due to the cam surface 36 in the illustrated embodiment, toward the proximal end 78 of the check valve 10. As described above, as this occurs the proximal end 64 of the post 60 pushes against the distal surface 88 of the diaphragm 30. However, the diaphragm 30 is prevented from moving in a proximal direction in its entirety, because at least a portion of the diaphragm 30 contacts the second shoulder 70 and thus is prevented from moving proximally. However, due to the force of the post 60, and the return force supplied by the second shoulder 70, the diaphragm 30 will be deformed in a distal direction with at least a central portion 92 of the proximal surface 84 of the diaphragm 30 being at least partially disposed within the first segment 74 of the first passageway 16.

As can be seen in FIGS. 2-2D and 2F, and with particular reference to FIGS. 2D and 2F, at least one bypass groove 94 is formed within the check valve 10 proximal to the diaphragm 30. In the illustrated embodiment, a plurality of bypass grooves 94 are depicted as disposed within the first segment 74 of the first passageway 16 and extending toward the second enlarged segment 76 of the first passageway 16. These bypass grooves 94 may be continuous and in fluid communication with the second passageway 20. These bypass grooves 94 may facilitate fluid flow from the second enlarged segment 76 of the first passageway 16, past the diaphragm 30, and to the first segment 74 of the first passageway 16. When the second body portion 18 is in a first position (as in FIGS. 2-2B and 2E), the bypass grooves 94 are blocked by the diaphragm 30. When the second body portion 18 is moved into the second position (such as by rotating the sleeve 34, in FIGS. 2C-2D and 2F), the diaphragm 30 is deformed such that the bypass grooves 94 are not blocked and fluid may flow therethrough. In particular, due to the deformation of the diaphragm 30 when the second body portion 18 is in the second position, the bypass grooves 94 are opened and span the area of the diaphragm 30. As described above, any attempted fluid flow in the second direction 28 occurs from the distal end 80 of the check valve 10 to the proximal end 78 of the check valve 10. When the second body portion 18 is disposed in the second position, the diaphragm 30 is deformed and the distal ends 96 of the bypass grooves 94 remain exposed, thus allowing fluid flow in the second direction 28 to flow past the diaphragm 30 and into the distal ends 96 of the bypass grooves 94. Fluid may then flow through the bypass grooves 94 and into the proximal portion 83 of the first passageway 16.

The check valve 10 of the present invention may further include a seal 100 disposed between the first body portion 14 and the second body portion 18. In one particular embodiment, this seal 100 may be provided by an O-ring 102. This O-ring 102 provides a fluid-tight seal 100 between the first body portion 14 and the second body portion 18 of the check valve 10. The seal 100 ensures that fluid will not escape the check valve 10.

The check valve 10 of the present invention may further include a spring 104 which may operate to bias the second body portion 18. In particular, the spring 104 may be positioned to bias the second body portion 18 to the first position. Thus, the spring 104 may be used to cause the diaphragm 30 to be in a normally closed position. In the illustrated embodiment, the O-ring 102 may function as the spring 104. However, it will be recognized by those of skill in the art that any spring 104, separate from an O-ring 102, may be used in accordance with the principles of the present invention. A spring 104 may be used, particularly in an embodiment that does not include a cam surface 36 on the sleeve 34. In such an embodiment, an operator would need to grasp and push the second body portion 18 in the proximal direction and manually hold the check valve 10 in that second position while fluid flows in the second direction 28. Once fluid flow in the second direction 28 is complete, the operator would release the grasp on the second body portion 18. The bias force of the spring 104 would then automatically force the second body portion 18 to return to the closed position. Such a configuration prevents the check valve 10 from inadvertently being left in the open position during an injection procedure.

Referring now to FIG. 3, in another aspect, the present invention may comprise an injection system 106. The injection system 106 may include a fluid output device 108 and a delivery tube 110 having a first end 112 and a second end 114. The first end 112 of the delivery tube 110 may be operatively connected to the fluid output device 108. A fluid input device 116 may be operatively connected to the second end 114 of the delivery tube 110. A check valve 10 may be operatively connected to the delivery tube 110 between the fluid input device 116 and the fluid output device 108. The check valve 10 may be adapted to be opened and closed manually.

The fluid input device 116 used in this aspect of the present invention may be any apparatus, such as medical apparatus, normally connected to delivery tubes 110 in fluid administration systems, such as a standard medical injection system 106. For example, in one particular embodiment of the present invention, the injection device 116 may include a syringe 42 having a plunger 40.

Further, in the injection system 106 of the present invention, the check valve 10 may be a check valve 10 as previously described above with respect to FIGS. 2-2F.

Referring now to FIGS. 4-7A, a second aspect of the present invention is shown. In this aspect, the present invention includes a connector 12 for a fluid administration system including a check valve 10 disposed within the connector 12. In particular, the connector 12 includes a housing 118 that defines at least a first fluid conduit 120, a second fluid conduit 122, and a third fluid conduit 134. The first fluid conduit 120 may be in fluid communication with the second fluid conduit 122. Either or both of the first fluid conduit 120 and the second fluid conduit 122 may be in fluid communication with the third fluid conduit 134. As it relates to the connector herein, the term "fluid communication" may mean that the first fluid conduit 120 and second fluid conduit 122 are disposed such that, should there be a first fluid and second fluid within the first and second fluid conduits 120, 122, those first and second fluids may confront one another in the first fluid conduit 120, in the second fluid conduit 122, or in an area proximal to the first and second fluid conduits 120, 122. Likewise, "fluid communication" also may mean that the third fluid conduit 134 is disposed within the housing 118 such that should there be a first fluid within the first fluid conduit 120 and/or a second fluid within the second fluid conduit 122, those first and second fluids may confront one another in the third fluid conduit 134, or in an area proximal to the third fluid conduit 134. A check valve 10 is disposed within the housing 118 and, in one embodiment, may be positioned at least partially within the first fluid conduit 120. However, it will be recognized that the check valve 10 alternatively may be disposed in the second fluid conduit 122 or, as in the illustrated embodiment, the check valve 10 may be disposed between the first fluid conduit 120 and the second fluid conduit 122. The check valve 10 of the connector 12 includes a diaphragm 30. The diaphragm 30 may move or alter in shape in order to vary between an open position and a closed position to allow or prevent fluid flow, respectively.

The check valve 10 is positioned within the housing 118 of the connector 12 in such manner as to eliminate dead zone on the exit side of the check valve 10. In particular, in an embodiment wherein the check valve 10 is positioned between the first fluid conduit 120 and the second fluid conduit 122, the distal end 80 of the check valve 10 may be positioned adjacent the second fluid conduit 122 in order to reduce or eliminate any space between the distal end of the check valve 10 and the second fluid conduit 122. This eliminates the collection of any air or a first fluid on the distal side of the check valve 10. More specifically, the check valve 10 may be positioned such that fluid flow from the first fluid conduit 120 enters the second fluid conduit 122 immediately after it passes the diaphragm 30. In particular, this is accomplished by positioning the diaphragm 30 at the intersection of the first fluid conduit 120 and the second fluid conduit 122. In such an embodiment, the proximal surface 84 of the diaphragm 30 is positioned immediately adjacent to the first fluid conduit 120, and the distal surface 88 of the diaphragm 30 is positioned adjacent the second fluid conduit 122. By having the diaphragm 30 positioned at the intersection of the first and second fluid conduits 120, 122, a first fluid within the first fluid conduit 120 may be introduced directly into a second fluid within the second fluid conduit 122. This configuration also eliminates the presence of a dead zone, since there is no space between the distal surface 88 of the diaphragm 30 and the second fluid conduit 122, and thus the collection of air or fluid adjacent distal surface 88 of the diaphragm 30 of the check valve 10 of the connector 12 is also eliminated. This configuration stands in stark contrast to prior art connectors which did not include check valves, and thus at least the entire first fluid conduit would constitute a dead zone.

In an embodiment, such as the illustrated embodiment, wherein the first and second fluid conduits 120, 122 are in fluid communication such that first and second fluids may confront one another in an area proximal to the first and second fluid conduits 120, 122, the diaphragm 30 may be positioned such that a first fluid within the first fluid conduit 120 may be directly introduced into the area proximal to the first and second fluid conduits 120, 122.

As described briefly above, the diaphragm 30 of the connector 12 of the present invention may be disposed in an open position or a closed position. In particular, when the diaphragm 30 is in the closed position, a first fluid, such as contrast media and/or air, may be prevented from accumulating proximal to the second fluid conduit 122. Such accumulation is prevented by positioning the check valve 10 within the connector 12, and particularly by positioning the diaphragm 30 adjacent the intersection point of the first and second fluid conduits 120, 122. The "intersection point" may include an area proximal to both of the first and second fluid conduits 120, 122. In particular, as first fluid is introduced into the first fluid conduit 120, it may fill the first fluid conduit 120 on the proximal side of the diaphragm 30 of the check valve 10. As the first fluid contacts the diaphragm 30, the fluid pressure will cause the diaphragm 30 to move or deform to allow first fluid to flow past and into fluid communication with the second fluid conduit 122. As the fluid pressure is reduced and eliminated, the diaphragm 30 will automatically close, leaving first fluid on the proximal side 84 of the diaphragm 30. However, once flushed through the fluid administration system, there is no first fluid remaining on the distal side 88 of the diaphragm and adjacent to or otherwise in fluid communication with the second fluid conduit 122. The second fluid conduit 122 may be filled with a second fluid. Thus, a second fluid may be introduced to a patient without being mixed with air or a first fluid. When the check valve 10 is placed in the open position due to fluid pressure being applied through the first fluid conduit 120, a first fluid may be introduced directly into fluid communication with the second fluid conduit 122.

As described above, the first fluid conduit 120 and second fluid conduit 122 may be in fluid communication. This fluid communication may be direct, wherein a portion of the first fluid conduit 120 opens directly into the second fluid conduit 122. Alternatively, and as in the illustrated embodiment, the fluid communication may be indirect. As can be seen in the figures, the housing 118 further defines a cavity 127. The distal portion 130 of the first fluid conduit 120 terminates into the cavity 127, and the distal portion 132 of the second fluid conduit 122 terminates into the cavity 127. The cavity 127 is further adapted to receive a plug 128. The plug 128 defines a plug conduit 129 which may receive fluid flow. Thus, the plug conduit 129 may be in fluid communication with either or both of the first fluid conduit 120 and the second fluid conduit 122. In particular, in the illustrated embodiment, a proximal end 131 of the plug conduit 129 is positioned adjacent to the second fluid conduit 122 and a distal end 133 of the plug conduit 129 opens to the cavity 127 proximal to the diaphragm 30. The plug further includes a nub 135 adapted to engage the diaphragm 30 when the plug 128 is received by the cavity 127. This nub 135 facilitates holding the diaphragm 30 in place within the connector 12.

Figure 5:
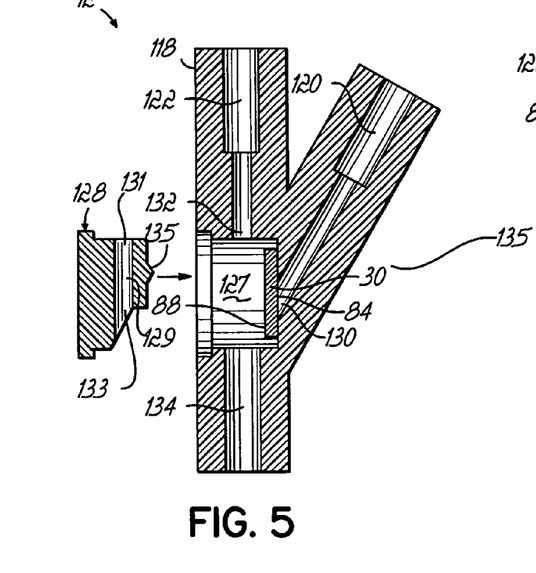
FIG. 5 is a cross-sectional side view of the connector, taken along line 5-5 of FIG. 4, with the plug of the connector removed, in accordance with the principles of the present invention.

As can be seen in the illustrated embodiment of FIG. 5, when the connector 12 includes a plug 128, the second fluid conduit 122 and third fluid conduit 134 are disposed on opposite sides of the plug cavity 127. However, it will be recognized that a connector 12 need not include a plug cavity 128. In such an embodiment, the second conduit 122 may be a segment of conduit disposed on one side of the intersection point between the first fluid conduit 120 and the second fluid conduit 122, and the third fluid conduit 134 may be a segment of conduit disposed on the opposite side of the intersection point.

Figure 6:
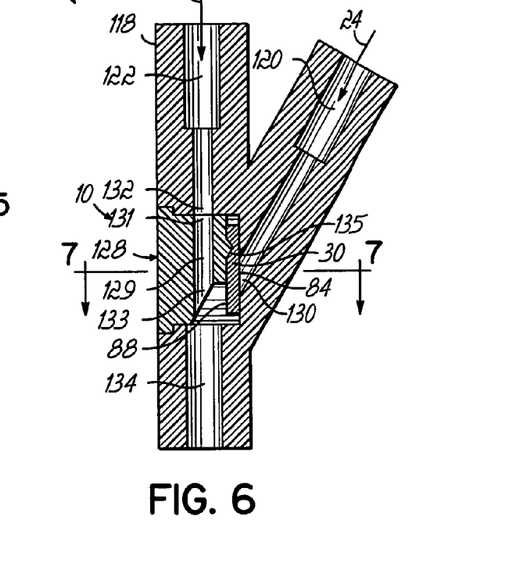
FIG. 6 is a side cross-sectional view of the connector, as in FIG. 5, with the plug of the connector inserted, in accordance with the principles of the present invention.

With particular reference to the embodiment illustrated in FIG. 6, while the diaphragm 30 is positioned within the connector 12 in such manner that it may deform in a distal direction to allow a first fluid to flow from the first fluid conduit 120 into the cavity 127 proximal the plug conduit 129, the diaphragm 30 is prevented from deforming in a proximal direction due to a connector shoulder 136 formed near the distal portion 130 of the first fluid conduit 120. This connector shoulder 136 blocks travel of the diaphragm 30 in the proximal direction.

Further still, it can be seen from FIGS. 4-7A that the housing 118 of the connector 12 of the present invention may further define a third fluid conduit 134. This third fluid conduit 134, in the illustrated embodiment, may be disposed beyond the first and second fluid conduits 120, 122 in the direction of forward fluid flow, and is in fluid communication with the first and second fluid conduits 120, 122. Once a first and/or a second fluid has progressed through the first and/or second fluid conduits 120, 122 respectively, it may progress thereon into the third fluid conduit 134 and ultimately to the fluid output device of a fluid administration system, and ultimately into a subject patient.

In one example of the use of the connector 12 of the present invention, contrast media may be used as the first fluid in the first fluid conduit 120, and saline may be used as the second fluid in the second fluid conduit 122 during a pre-scan. However, due to the normally closed status of the check valve 10, the first fluid contrast media is prevented from introduction into the second fluid conduit 122 unless and until sufficient pressure is applied to the check valve 10 to displace the diaphragm 30 and allow the first fluid to flow into the second fluid conduit 122. Prior to the application of pressure to displace the diaphragm 30, the second fluid saline may be injected into a patient in order to perform a pre-scan. Due to the check valve 10, the first fluid, contrast media, is prevented from introduction into the saline. Thus the image during a scan will not be degraded.

Further, as described above, due to the fact that at least a portion of the check valve 10, including the diaphragm 30 at the distal end 80 thereof, projects into or is located adjacent to the second fluid conduit 122, there is no dead zone area where air or other fluid may collect. This prevents the introduction of air to the patient body which, as described above, can be extremely problematic. The check valve 10 also prevents the premature introduction of the first fluid into the second fluid conduit 122, which in the case of contrast media, can cause image degradation, as described above.

Once the pre-scan procedure involving the use of saline is complete, positive pressure may be applied to the first fluid conduit 120. Such positive pressure may be applied by depressing a plunger 40 of a syringe 42 that is operatively connected to the first fluid conduit 120. The pressure caused the diaphragm 30 to displace from the closed to the opened position, thereby allowing introduction of the first fluid directly into the second fluid conduit 122. The diaphragm 30 may be a flexible diaphragm which deforms upon the pressure of fluid flow. Alternatively, as in the illustrated embodiment, deformation of the diaphragm 30 may allow first fluid to be introduced into the cavity 127 and plug conduit 129, and thereafter into third fluid conduit 134.

Figure 7:
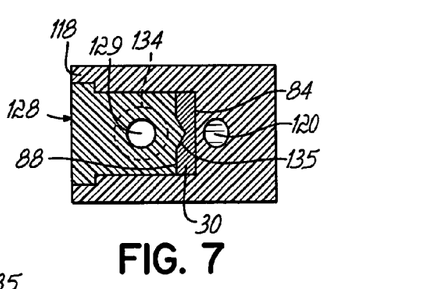
FIG. 7 is an end cross-sectional view of the plug of the connector taken along line 7-7 of FIG. 6, in accordance with the principles of the present invention.
Figure 7A:
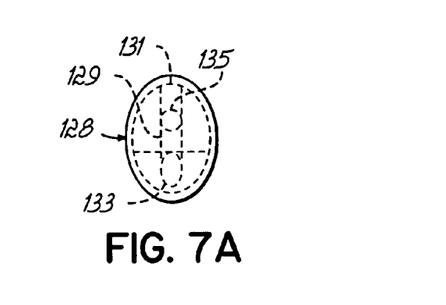
FIG. 7A is a top view of the elliptical diaphragm of the connector, in accordance with the principles of the present invention.

In the particular illustrated embodiment of the present invention, the diaphragm 30 may be of an elliptical shape (see FIG. 7A). This elliptical shape allows the overall size of the connector 12 to be reduced. The smaller size of the connector 12 provides many benefits, such as better appearance, less material to produce, and less cost to produce. The plug 128 of the connector 12 may also be of an elliptical shape, as shown in the illustrated embodiment. This shape of the plug 128 also results in the same benefits recited above with respect to an elliptical diaphragm 30. The check valve 10, in one embodiment, may be configured such as that described above with respect to FIGS. 2-2F.

The connector 12 of the present invention may be made of any materials that are commonly used to make standard connectors 12. These materials include, but are not limited to, polyurethanes, polypropanes and polyolefins.

Figure 8:
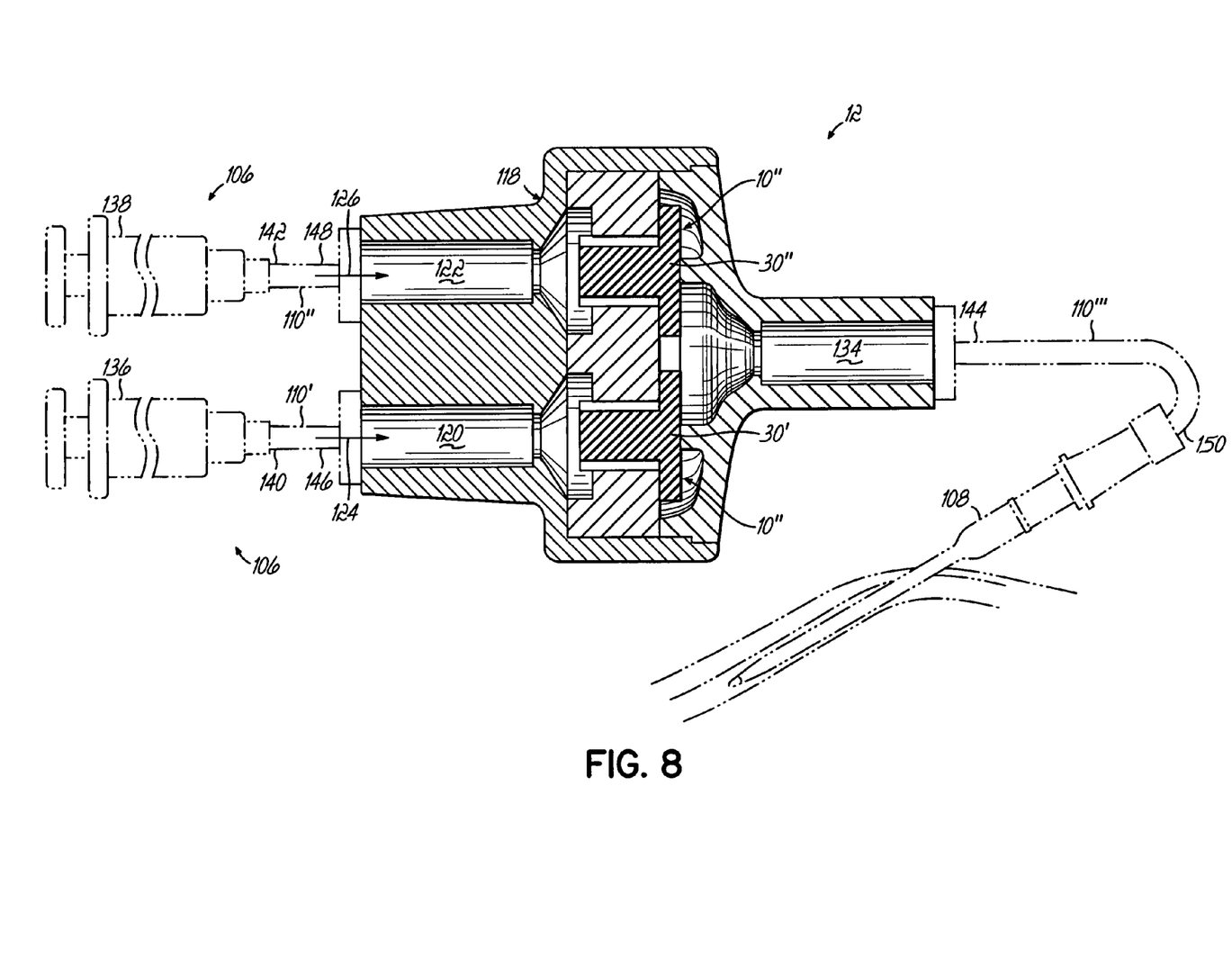
FIG. 8 is a cross-sectional view of a connector including multiple check valves, in accordance with the principles of the present invention.
Figure 8A:
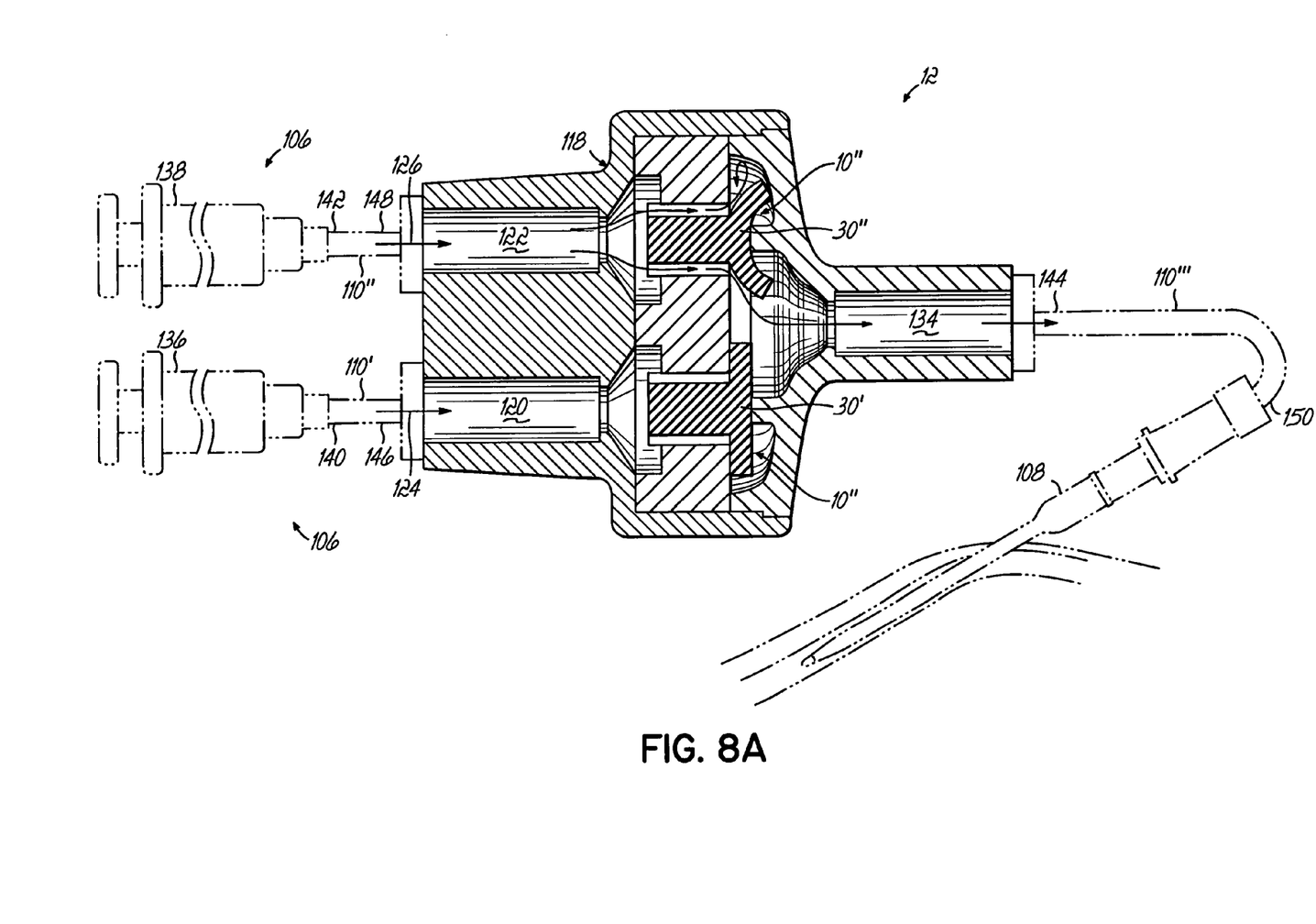
FIG. 8A is a cross-sectional view of a connector, as in FIG. 8, with fluid flow in a forward direction, in accordance with the principles of the present invention.

Alternatively, and referring now to FIGS. 8-8A, the connector 12 may further include a plurality of check valves disposed within the housing 118. The connector 12 of this embodiment of the present invention includes a housing 118 and first, second, and third fluid conduits 120, 122, 134 defined by the housing 118. In this embodiment, the first fluid conduit 120 is disposed such that it interacts with and is in fluid communication with the third fluid conduit 134. The second fluid conduit 122 is disposed such that it interacts with and is in fluid communication with the third fluid conduit 134. In particular, a first check valve 10' may be positioned within the fluid flow of the first fluid conduit 120, and a second check valve 10" may be positioned within the fluid flow of the second fluid conduit 122. The exit end of the first check valve 10' may be positioned directly into the third fluid conduit 134. The exit end of the second check valve 10" may be positioned within the fluid flow of the third fluid conduit 134. In particular, this is accomplished by having a first diaphragm 30' positioned at the intersection of the first and third fluid conduits 120, 134 and a second diaphragm 30" positioned at the intersection of the second and third fluid conduits 122, 134. Each of the first and second check valves 10', 10" may be movable between a closed and an open position. As a result, the introduction of a first fluid, such as contrast media, may occur by being directly injected into a second fluid, such as saline. Additionally, air can be removed from the system while not exposing contrast to the saline. The use of first and second check valves 10', 10" also allows for the use of fluid administration devices, such as plungers 42, operatively connected to the first and second fluid conduits 120, 122 that have differing pressure ratings. The presence of the check valves 10 closes off and separates the first and second fluid conduits 120, 122 so as to prevent the pressure from one syringe 42 from affecting another syringe 42 or fluid conduit.

The connector 12 of this embodiment of the present invention may be made of any materials that are commonly used to make standard connectors 12. These materials include, but are not limited to, polyurethanes, polypropanes and polyolefins. Further, in the illustrated embodiment, both the first and second fluid conduits 120, 122 are shown as being disposed in a manner that is substantially parallel to the third fluid conduit 134. However, it will be recognized by those of skill in the relevant art that this configuration is merely exemplary, and that the first and second fluid conduits 120, 122 may be disposed at any angle relative to the third fluid conduit 134 that would allow the connector 12 to remain functional for the purposes in accordance with the principles of the present invention. Such determination is well within the knowledge of one skill in the art.

The first and second check valves 10', 10" of the connector 12 of the embodiment of the present invention illustrated in FIGS. 8-8A may be disposed in an open position or a closed position. In particular, when either check valve 10', 10" is in the closed position, a fluid, such as contrast media, saline, and/or air, may be prevented from accumulating within the third fluid flow conduits proximal to either check valve 10', 10". Alternatively, when either check valve 10', 10" is in the open position, a first fluid, such as contrast media, may be introduced directly into the third fluid conduit 134, or into a second fluid, such as saline, within the third fluid conduit 134.

Referring in particular to FIGS. 8-8A, the first and second check valves 10', 10" in the illustrated embodiment of the connector 12 of the present invention each include a diaphragm 30. As can be seen in the illustrated embodiment of the present invention, a first diaphragm 30' is positioned at the point in the connector 12 where the first fluid conduit 120 and the third fluid conduit 134 intersect. Additionally, a second diaphragm 30" is positioned at the point in the connector 12 where the second fluid conduit 122 and the third fluid conduit 134 intersect. These locations will be referred to as the "intersection points" herein.

In a further embodiment, the present invention may include an injection system 106 including a connector 12 having at least one check valve 10, as described above. The injection system 106 may include a connector 12 having a plurality of check valves 10. Any connector typically used in such injection systems may be used in the injection system 106 of the present invention. In one particular embodiment, a Y-connector may be used.

Thus, the injection system 106 of the present invention includes first and second administration devices 136, 138, first, second, and third delivery tubes, 110', 110", and 110''' and a connector 12 having at least one check valve 10. Each delivery tube 110', 110", and 110''' includes proximal ends 140, 142, 144 and distal ends 146, 148, 150. The proximal end 140 of the first delivery tube 110' is operatively connected to the first injection device 116. The distal end 146 of the first delivery tube 110' is operatively connected to the first fluid conduit 120 of the connector 12. The proximal end 144 of the third delivery tube 110''' is operatively connected to the third fluid conduit 134. The distal end 150 of the third delivery tube 110''' is operatively connected to an output, such as a catheter 108. The connector 12 may further comprise a Y-connector including a housing 118 and first and second fluid conduits 120, 122 defined by the housing 118, wherein the first conduit 120 is disposed at an angle relative to and interacting with the second conduit 122; and a check valve 10 disposed within the housing 118 and positioned within the fluid flow of the first conduit 120, the check valve 10 being movable between an open and a closed position.

While the present invention has been disclosed by reference to the details of preferred embodiments of the invention, it is to be understood that the disclosure is intended as an illustrative rather than in a limiting sense, as it is contemplated that modifications will readily occur to those skilled in the art, within the spirit of the invention and the scope of the amended claims.

What is claimed is:

1. A connector for a fluid administration system, the connector comprising:
   a housing;
   a first conduit, a second conduit, and a third conduit defined by said housing, wherein said first conduit is in fluid communication with said second conduit, and each of said first conduit and said second conduit is in fluid communication with said third conduit; and
   at least a first check valve disposed within said housing, said first check valve including a first diaphragm having an elliptical shape.

2. The connector of claim 1, wherein at least a portion of said first check valve is disposed within said first conduit.

3. The connector of claim 1, wherein said first check valve is disposed between said first conduit and said second conduit.

4. The connector of claim 2, wherein said first diaphragm includes a proximal surface and a distal surface, said distal surface being adjacent to said second conduit.

5. The connector of claim 3, wherein said first diaphragm includes a proximal surface and a distal surface, said proximal surface being adjacent to said first conduit and said distal surface being adjacent to said second conduit.

6. The connector of claim 1, wherein said first conduit is adapted to transport a first fluid.

7. The connector of claim 6, wherein said second conduit is adapted to transport a second fluid.

8. The connector of claim 7, wherein said first diaphragm is movable between an opened position and a closed position.

9. The connector of claim 8, wherein said first fluid communicates with said second conduit when said first diaphragm is in said opened position.

10. The connector of claim 8, wherein said first fluid is prevented from communicating with said second conduit when said first diaphragm is in said closed position.

11. The connector of claim 8, wherein said housing further defines a cavity adapted to receive a plug.

12. The connector of claim 11, further comprising a plug disposed within said cavity.

13. The connector of claim 12, wherein said plug further defines a plug conduit in fluid communication with said first conduit and said second conduit.

14. The connector of claim 13, wherein said first fluid communicates with said plug conduit when said first diaphragm is in said opened position.

15. The connector of claim 12, wherein said plug is elliptical.

16. The connector of claim 1, further comprising a second check valve disposed within said housing.

17. The connector of claim 16, said second check valve including a second diaphragm and said second check valve being at least partially disposed within second conduit.

18. The connector of claim 16, said second check valve including a second diaphragm and said second check valve being disposed between said second conduit and said third conduit.

19. The connector of claim 16, wherein said first diaphragm of said first check valve includes a proximal surface and a distal surface, said distal surface being adjacent to, said third conduit.

20. The connector of claim 19, wherein said second check valve includes a second diaphragm, said second diaphragm including a proximal surface and a distal surface, said distal surface being adjacent to said third conduit.

21. The connector of claim 8, wherein said first diaphragm is flexible.

22. The connector of claim 21, wherein said first diaphragm is adapted to deform in the distal direction into said open position wherein said first fluid communicates with said second conduit.

23. A fluid administration system, comprising:
   a fluid input device;
   a fluid output device operatively connected to said fluid input device;
   a housing defining a first conduit, a second conduit, and a third conduit, wherein said first conduit is in fluid communication with said second conduit, and each of said first conduit and said second conduit is in fluid communication with said third conduit; and
   a check valve disposed within said fluid administration system, said check valve selectively adaptable to allow flow of a fluid or not allow flow of a fluid from said fluid output device to said fluid input device through or past said check valve, and said check valve including a diaphragm having an elliptical shape.

24. The fluid administration system of claim 23, wherein the check valve comprises:
   a first body portion defining a first passageway for fluid flow; and
   a second body portion defining a second passageway for fluid flow, said second body portion adapted to be in receiving relationship with said first body portion such that said first passageway and said second passageway are in fluid communication with one another, and wherein said second body portion is movable relative to said first body portion between a first position and a second position;
   wherein when said second body portion is in said first position, fluid flow may occur in a first direction, but not in a second direction, said second direction being substantially opposite to said first direction, and when said second body portion is in said second position, fluid flow may occur in said second direction.

25. The fluid administration system of claim 24, wherein said diaphragm is disposed between said first body portion and said second body portion in the path of fluid flow, said diaphragm being movable between an open position and a closed position.

26. The fluid administration system of claim 25, further including a sleeve substantially surrounding a portion of said second body portion, said sleeve including a cam and said sleeve being positionable in an engaged position or a disengaged position.

27. The fluid administration system of claim 26, wherein when said sleeve is in said first position, said sleeve is in confronting relationship with said first body portion and operates counter to and creates a force greater to the bias of said spring, such that said connector is in confronting relationship with said diaphragm and said diaphragm is in said closed position.

28. The fluid administration system of claim 27, wherein when said sleeve is in said second position, said sleeve is not in confronting relationship with said first body portion, such that said spring biases said connector such that said connector is not in confronting relationship with said diaphragm and said diaphragm is in said open position.

29. The fluid administration system of claim 28, wherein said diaphragm is flexible.

30. The fluid administration system of claim 29, wherein a proximal end of said second body portion is adjacent said diaphragm when said second body portion is in said first position.

31. The fluid administration system of claim 30, wherein said proximal end of said second body portion contacts and confronts said diaphragm to deform said diaphragm into the open position toward the proximal end of the check valve, when said second body portion is in said second position.

32. The fluid administration system of claim 28, wherein said check valve further includes at least one bypass groove.

33. The fluid administration system of claim 32, wherein said at least one bypass groove is disposed in said first passageway and is adapted to be in fluid communication with said second passageway.

34. The fluid administration system of claim 33, wherein said at least one bypass groove is in fluid communication with said second passageway when said diaphragm is in said open position.

35. The fluid administration system of claim 34, wherein said at least one bypass groove is not in fluid communication with said first passageway when said diaphragm is in said closed position.

36. The fluid administration system of claim 24, further comprising a seal disposed between said first body portion and said second body portion.

37. The fluid administration system of claim 36, wherein said seal includes an O-ring.

38. The fluid administration system of claim 26, further comprising a spring operatively connected to said second body portion, said spring positioned to bias said second body portion away from said first body portion.

39. A fluid administration system, comprising:
a fluid input device;
a first delivery tube having first and second ends, said first end of said first delivery tube being operatively connected to said fluid input device;
a connector further comprising a housing, first, second, and third conduits defined by said housing, wherein said first conduit is in fluid communication with said second conduit and each of said first conduit and said second conduit is in fluid communication with said third conduit, and a check valve disposed within said housing, said check valve including a diaphragm having an elliptical shape, and said second end of said first delivery tube being operatively connected to said connector;
a second delivery tube having first and second ends, said first end of said second delivery tube being operatively connected to said connector; and
a fluid output device operatively connected to said second end of said second delivery tube.

40. The fluid administration system of claim 39, wherein at least a portion of said check valve is disposed within said first conduit.

41. The fluid administration system of claim 39, wherein said check valve is disposed between said first conduit and said second conduit.

42. The fluid administration system of claim 39, wherein said diaphragm includes a proximal surface and a distal surface, said distal surface being adjacent to said second conduit.

43. The fluid administration system of claim 42, said proximal surface being adjacent to said first conduit.

44. The fluid administration system of claim 39, wherein said diaphragm is movable between an opened position and a closed position.

45. The fluid administration system of claim 39, wherein said check valve further comprises:
a first body portion defining a first passageway for fluid flow; and
a second body portion defining a second passageway for fluid flow, said second body portion adapted to be in receiving relationship with said first body portion such that said first passageway and said second passageway are in fluid communication with one another, and wherein said second body portion is movable relative to said first body portion between a first position and a second position;
wherein when said second body portion is in said first position, fluid flow may occur in a first direction, but not in a second direction, said second direction being substantially opposite to said first direction, and when said second body portion is in said second position, fluid flow may occur in said second direction.

46. The fluid administration system of claim 45, wherein said diaphragm is disposed between said first body portion and said second body portion in the path of fluid flow, said diaphragm being movable between an open position and a closed position.

* * * * *

UNITED STATES PATENT AND TRADEMARK OFFICE
CERTIFICATE OF CORRECTION

PATENT NO. : 7,581,559 B2  Page 1 of 1
APPLICATION NO. : 10/794358
DATED : September 1, 2009
INVENTOR(S) : William E. Bausmith, III It is certified that error appears in the above-identified patent and that said Letters Patent is hereby corrected as shown below:

In line 10 of the abstract in the second column of the cover page, before "second", delete "a".

In column 1, line 6-7, change "valves, and" to --valves and,--.

In column 5, line 19, after "embodiment", insert --of the--.

In column 6:
Line 28, change "lines" to --line--
Line 31, change "section-section" to --cross-section-- and change "lines" to --line--.

In column 11, line 9, change "is" to --are--.

In column 16, line 21, change "skill" to --skilled--.

In column 17, line 10, change "amended" to --appended--.

In column 18, line 3, after "to" delete ",".

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

PATENT NO.       : 7,581,559 B2                                            Page 1 of 1
APPLICATION NO.  : 10/794358
DATED            : September 1, 2009
INVENTOR(S)      : William E. Bausmith, III It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 449 days.

Signed and Sealed this

Fourteenth Day of December, 2010

David J. Kappos
*Director of the United States Patent and Trademark Office*